United States Patent
Lafferty

(10) Patent No.: US 11,850,123 B2
(45) Date of Patent: Dec. 26, 2023

(54) METHOD FOR DRESSING WOUNDS WITH CHROMIC MATERIALS

(71) Applicant: Isabella R Lafferty, Cumming, GA (US)

(72) Inventor: Isabella R Lafferty, Cumming, GA (US)

( * ) Notice: Subject to any disclaimer, the term of this patent is extended or adjusted under 35 U.S.C. 154(b) by 826 days.

(21) Appl. No.: 16/870,922

(22) Filed: May 9, 2020

(65) Prior Publication Data
US 2020/0268559 A1    Aug. 27, 2020

(51) Int. Cl.
*A61F 13/00*    (2006.01)

(52) U.S. Cl.
CPC .. *A61F 13/00059* (2013.01); *A61F 13/00008* (2013.01); *A61F 13/00034* (2013.01)

(58) Field of Classification Search
CPC ...... A61L 15/42; A61L 2400/04; A61L 15/60; A61L 15/44; A61F 2013/00638; A61F 2013/0054; A61F 2013/00685; A61F 2013/00463; A61F 13/00021; A61F 13/00034; A61F 13/00008; A61F 13/00059
See application file for complete search history.

(56) References Cited

U.S. PATENT DOCUMENTS

| | | |
|---|---|---|
| 8,828,050 B2 | 9/2014 | Gregory et al. |
| 2008/0128932 A1 | 6/2008 | Hopman |
| 2010/0029004 A1 | 2/2010 | Ribi |
| 2013/0022552 A1 | 1/2013 | Solomon |
| 2014/0142523 A1 | 5/2014 | Steinbaugh |
| 2014/0180229 A1 | 6/2014 | Fuller |
| 2017/0003257 A1 | 1/2017 | Klofta |
| 2018/0071149 A1 | 3/2018 | Barofsky |
| 2019/0209389 A1 | 7/2019 | Jacobs |
| 2019/0247458 A1 | 8/2019 | Norchi |

OTHER PUBLICATIONS

Hadi Khoshmohabat ey al. article titled "Overview of Agents Used for Emergency Hemostasis" Trauma Monthly, from https://www.ncbi.nlm.nih.gov/pmc/articles/PMC4869418/ Year:2016.
Songshan Zeng, Multi-Stimuli Responsive Chromism With Tailorable Mechanochromic Sensitivity For Versatile Interactive Sensing Under Ambient Conditions, The Royal Society of Chemistry, 2019, 9 pages.

*Primary Examiner* — Ophelia A Hawthorne

(57) ABSTRACT

A method for dressing a wound. The method includes introducing a chromic material via at least one article to the wound and stimulating the chromic material with a stimuli. The method also includes providing a color change in response to stimulating the chromic material and indicating via the color change of the chromic material how long the article has been at least partially in contact with the wound. In one or more embodiments, the method may also include measuring the color change from information including a plurality of colors corresponding to a plurality of time periods and, in response to measuring the color change, determining a length of time the article has been in contact with the wound. The method may also include manually crumpling a distal end of a portion of the article such that the distal end of the portion is sized to be received within the wound and then manually separating the crumpled distal end from the rest of the article.

18 Claims, 12 Drawing Sheets

METHOD FOR DRESSING WOUNDS WITH CHROMIC MATERIALS

CROSS REFERENCE TO RELATED APPLICATION

The present U.S. nonprovisional application is related to U.S. nonprovisional application entitled "CHROMISM FOR HEMORRHAGE CONTROL (A1001)", which is incorporated herein by reference, and having been filed concurrently with the present application.

TECHNICAL FIELD

The present invention generally relates to dressing wounds and controlling bleeding and, more specifically, utilizing color change phenomena of chromic materials to treat wounds.

BACKGROUND

Emergency medical professionals treat a myriad of wounds such as battlefield wounds, civilian gun and knife violence, automobile accidents and more. However, the first medical professional to treat the injury is usually not the last to treat the patient. Also, a significant amount of time often elapses between when the injury is initially stabilized and then when that same injury is subsequently treated with more specific and extensive treatment. Thus, because of the number of medical personnel that could be involved with a patient and then the length of time a particular wound may need to be treated, many such patients may be harmed because information related to the hemorrhage control is not available, has not been shared, or is insufficient. Thus, these limitations diminish the usefulness of existing hemorrhage control devices and methods.

SUMMARY

According to a non-limiting embodiment, a method of dressing a wound is provided. The method includes introducing a chromic material via at least one article to the wound and stimulating the chromic material with a stimuli. The method also includes providing a color change in response to stimulating the chromic material and indicating via a color change of the chromic material how long the at least one article has been at least partially in contact with the wound. In some embodiments, the article includes an elongated member defining a plurality of individual liquid expandable articles, where the method includes manually crumpling a distal end of the elongated member such that a portion of the plurality of individual liquid expandable articles are sized to be received within the wound.

According to another non-limiting embodiment, a method for dressing a puncture wound includes introducing a chromic material via at least one article to the puncture wound and stimulating the chromic material with a stimuli. The method also includes providing a color change in response to stimulating the chromic material and providing a first color change of the chromic material in response to initial contact of the at least one article with the puncture wound and then subsequently providing a second color change of the chromic material in response to prolonged contact of the at least one article with the wound.

According to another non-limiting embodiment, a method for dressing a puncture wound includes introducing a chromic material via at least one article to the puncture wound and stimulating the chromic material with a stimuli. The method also includes providing a first color change of the chromic material in response to initial contact of the at least one article with the puncture wound and then subsequently providing a second color change of the chromic material in response to prolonged contact of the at least one article with the puncture wound. The method then includes manually crumpling a distal end of a portion of the at least one article such that the distal end of the portion is sized to be received within the puncture wound and manually separating the crumpled distal end from another portion of the at least one article not within the puncture wound. The method also includes measuring color changes of the chromic material from information comprising a plurality of colors corresponding to a plurality of time periods and, in response, determining a length of time the at least one article has been in contact with the puncture wound.

Additional features and advantages are realized through the techniques of the invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
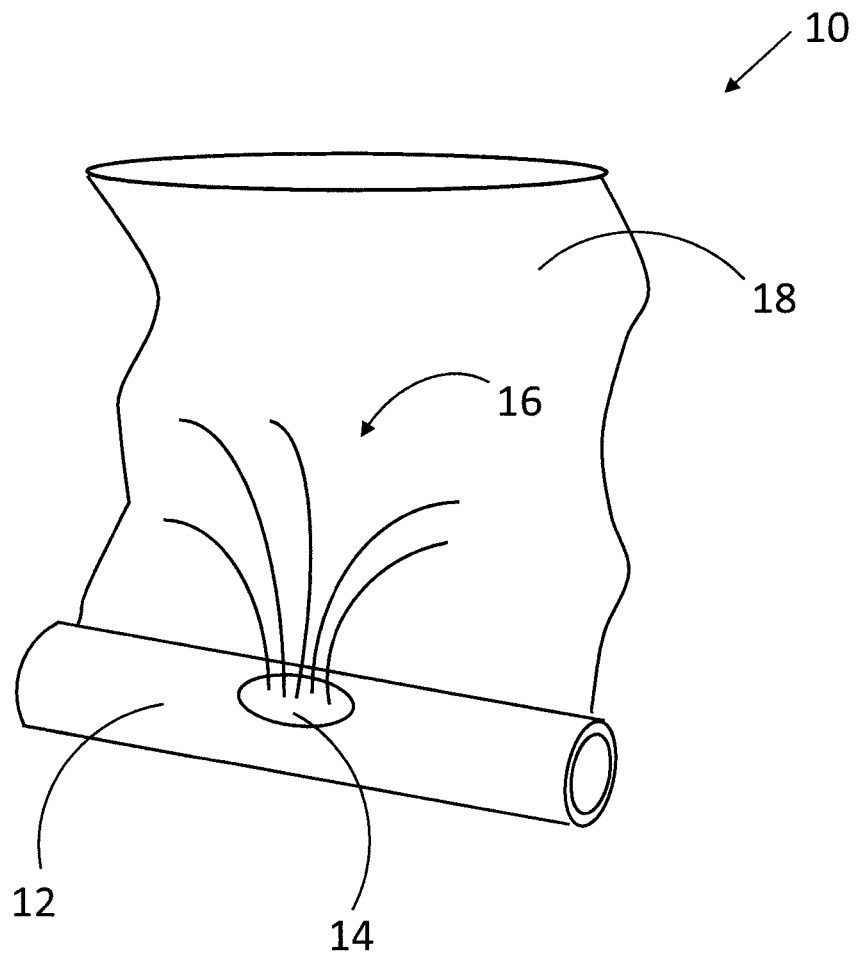
FIG. 1 depicts a generalized exemplary embodiment of a puncture wound for describing one or more embodiments of the invention.

The diagrams depicted herein are illustrative. There can be many variations to the diagram or the operations described therein without departing from the spirit of the invention. For instance, the actions can be performed in a differing order or actions can be added, deleted or modified. All of these variations are considered a part of the specification.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Figure 2:
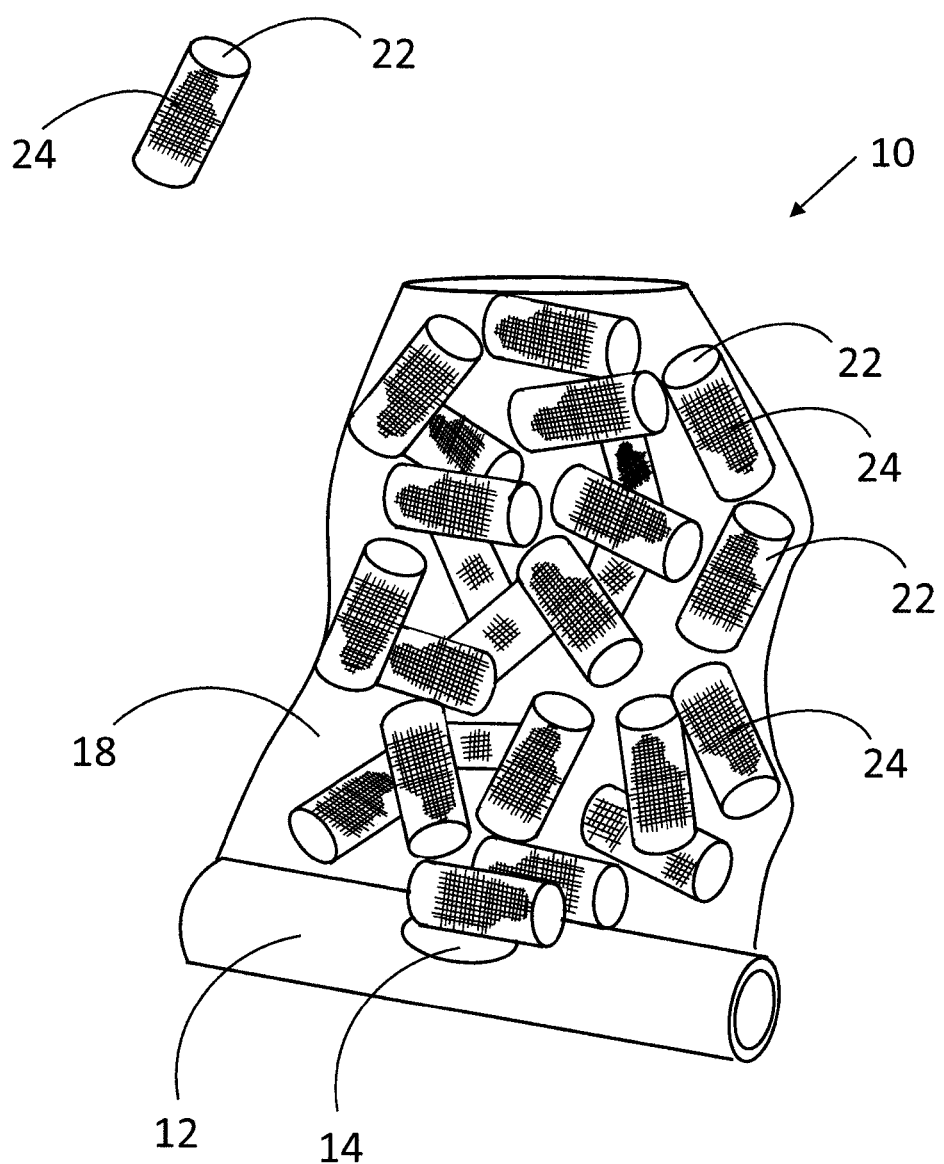
FIG. 2 depicts a plurality of articles with chromic material within the puncture wound of FIG. 1 according to one or more embodiments of the invention.

FIG. 1 illustrates an exemplary wound 10 where a blood vessel 12 has an opening 14 from which blood 16 leaks into a cavity 18. The wound 10 may be any type of wound such as, for example, but not limited to, an open wound or puncture wound where pressure and stoppage of bleeding is desirable. Referring to FIG. 2, the wound 10 is illustrated with a plurality of articles 22 for applying pressure and stopping the bleeding from the blood vessel 12. The articles 22 may be of any suitable material capable of coming into direct contact with the wound 10. For example, an article may be, but not limited to, a wound dressing such as cloth, foam, powder, clear film for transparent dressings, hydrocolloid dressings, hydrogel, alginate, and collagen.

In one or more embodiments, the articles 22 are liquid-expandable articles which expand upon contact with a liquid such as blood or other liquids used with wounds by medical professionals such as disinfectants, clotting agents and the like. All or some of the articles 22 may be the same size and shape or some or all may be sized and shaped differently in order to conform to irregular wounds, be received within a wound, or placed in contact with a wound.

Still referring to FIG. 2, the articles 22 may be absorbent material including, but not limited to sponges, cellulose or some other absorbent material. In one or more embodiments, the articles 22 may be compressed or configured to expand such that when received inside the wound 10 the articles 22 release stored mechanical energy and mechanically expand into expanded articles 30, as shown in FIG. 3, upon contact with liquid inside the wound 10.

Figure 3:
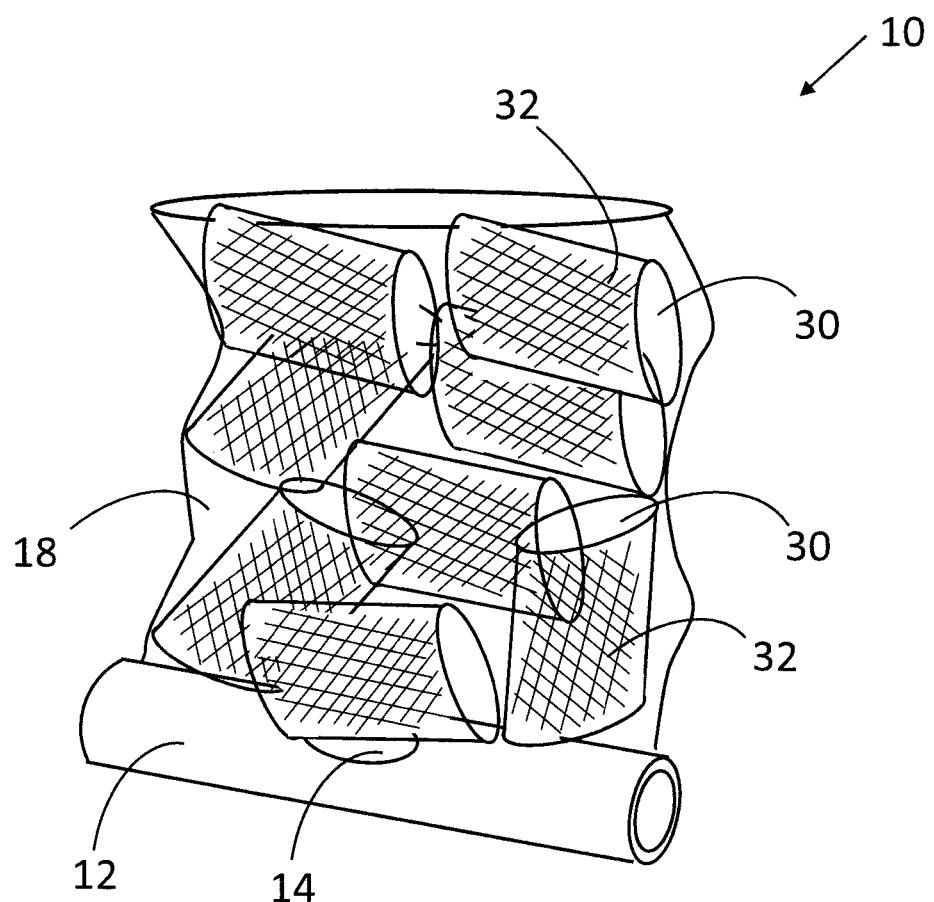
FIG. 3 depicts the plurality of articles of FIG. 2 expanded within the puncture wound of FIG. 1 where the chromic material has experienced a color change according to one or more embodiments of the invention.

Referring to FIGS. 2 and 3, the articles 22 include a chromic material 24 responsive to at least one stimuli. Some chromic materials 24 are responsive to more than one stimuli. The articles 22 are preferable configured to introduce the chromic material 24 to and/or dress the wound 10. The chromic material 24 may be placed on, soaked on, or sprayed on the surface or the interior of one or more or all of the articles 22 in any suitable manner sufficient for then allowing stimuli to affect the chromic material 24.

As a result of the stimuli affecting the chromic material 24, the chromic material 24 provides a visual indicator, directly discernable by the naked eye, indicating the at least one article is at least partially in contact the wound 10. In one or more embodiments, the indicator indicates how long at least one article has been at least partially in contact with the wound 10 and/or where the at least one article is placed within the wound 10. The indicator may be a color change evidencing where the at least one article has been placed within the wound 10 or the indictor may be a color change indicating a period of time associated with how long the at least one article has been in contact with the wound 10. In one or more embodiments, the indicator is a first color corresponding with a first period of time and then changes to a second color corresponding with a second period of time. For example, the articles 22 in FIG. 2 have chromic material 24 with a first color corresponding with the initial contact with the wound 10 for the first period of time and, as depicted in FIG. 3, the articles 22 have expanded into expanded articles 30 having chromic material 32 with a second color corresponding with the second period of time. The chromic material 32 in FIG. 3 has changed color due to stimuli such as blood causing expansion of articles 32 within wound 10. In one or more embodiments, because the temperature within a wound varies over time due to healing and variations in the amount of blood present, the indictor is reversible such that the indicator changes from the first color to the second color and then reverts back to the first color later in time compared to the second period of time.

Suitable chromic materials for the indicator are those which involve a change in color as a result of one or more stimuli and that are sometimes referred to as chromisms which may include, but is not limited to: Photochromism (color change caused by light), Thermochromism (color change caused by temperature (heat)), Solvatochromism (color change caused by solvent polarity), Vapochromism (color change caused by vapor of an organic compound due to chemical polarity/polarization), Ionochromism (change caused by ions), Halochromism (color change caused by a change in pH), Piezochromism (color change caused by mechanical pressure), Biochromism (color change caused by interfacing with a biological entity), Cryochromism (color change caused by lowering of temperature), Hydrochromism (color change caused by interaction with bulk water or humidity) and Chronochromism (color change indirectly as a result of the passage of time).

There are also multi-stimuli responsive chromic materials which exhibit a color change when exposed to two or more stimuli. For example, thermochromic and photochromic effects can be achieved simultaneously by homogenously mixing powders with appropriate color changing style selection and proper mass ratio as disclosed in "Multi-Stimuli Responsive Chromism With Tailorable Mechanochromic Sensitivity For Versatile Interactive Sensing Under Ambient Conditions" by Songshan Zeng et al., The Royal Society of Chemistry, 2019, which is hereby incorporated by reference in its entirety. Thus, a chromic material introduced to a wound 10 responsive to a plurality of stimuli such as, for example, heat and light, can be utilized to indicate how long an article has been in contact with the wound 10.

For example, thermochromic materials change color due to a change in temperature and can be used while treating wounds and wound healing because the temperature of a wound varies over time, for example, over a period of minutes, hours or over a period of days, especially while healing. In one or more embodiments, the thermochromic material changes color due to the temperature or the temperature change over time of the blood of the wound 10. Thermochromatic crystals and leuco dyes are capable of displaying different colors at different temperatures. For example, the color of thermochromic liquid crystals can continuously range from non-reflective (black) through the spectral colors to black again depending on the temperature. Some thermochromic liquid crystals are cholesteryl nonanoate or cyanobiphenyls. Mixtures with 3 to 5 degrees C. span of temperatures and ranges from about 17 to 23 degrees C. to about 37 to 40 degrees C. can be composed from varying portions of cholesteryl oleyl carbonate, cholesteryl nonanoate, and cholesteryl benzoate. For example, the mass ratio of 65:25:10 yields a range of 17 to 23 degrees C. and 30:60:10 yields a range of 37 to 40 degrees C.

Suitable leuco dyes include spirolactones, fluorans, spiropyans and fulgides. Acids which include bisphenol A, parabens, 1,2,3-triazole derivatives, and 4-hydroxycoumarin act as proton donors, changing the dye molecule between its leuco form and its protonated colored form. Stronger acids will make the color change irreversible which facilitates temperature change determinations. Also, organic leuco dyes are available for temperature ranges between minus 5 degrees C. and 60 degrees C. in a wide range of colors.

In one or more embodiments, the chromic material is thermochromic and the indicator is a color change caused by temperature as the at least one stimuli. For example, the article may be a clotting agent where the color change is caused by heat generated by the clotting agent reacting with a liquid associated with the wound such as blood. In one or more other embodiments, the chromic material is chronochromic and the indicator is caused by how long the chromic material has been in contact with the liquid. In other words, the color change of the chromic material is caused by the passage of time.

Figure 4A:
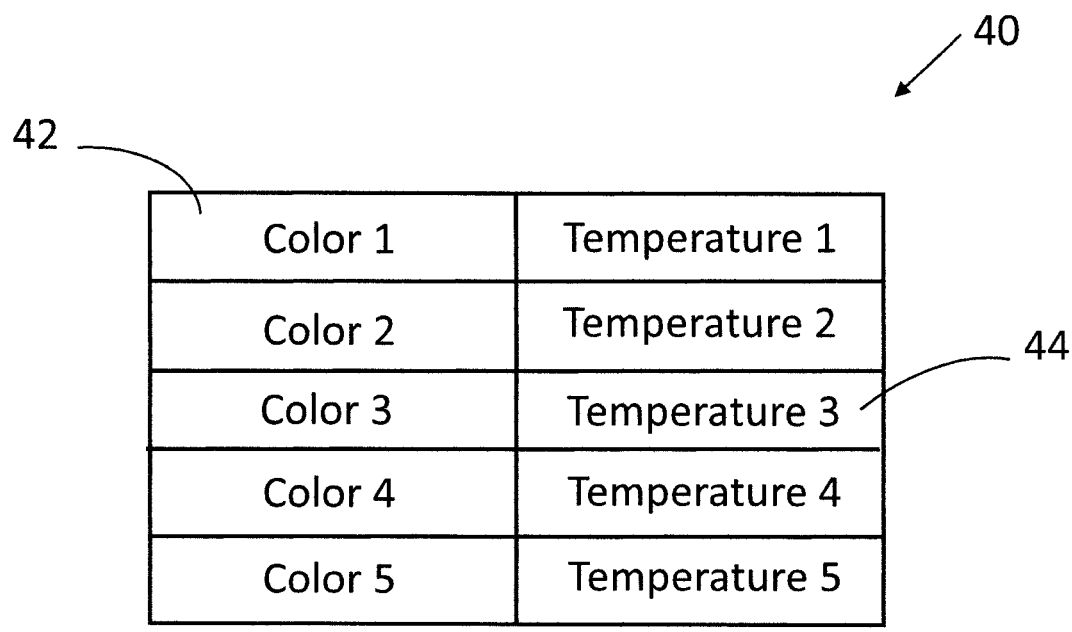
FIGS. 4A and 4B depict exemplary embodiments of information for measuring color change of the chromic material according to one or more embodiments of the invention.
Figure 4B:
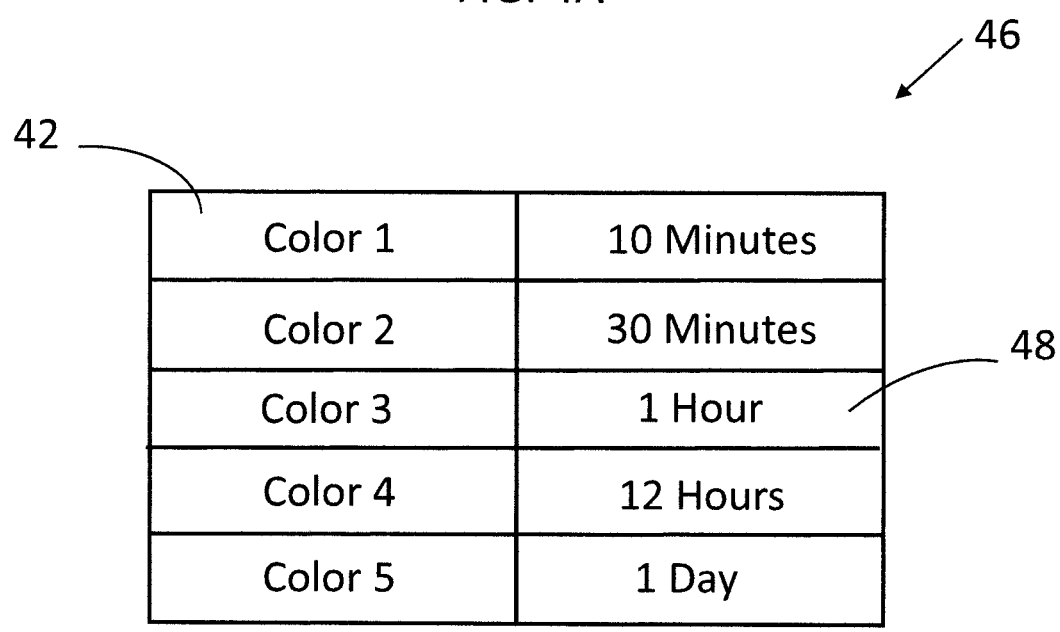

One or more embodiments may include a kit for dressing a wound 10. The kit includes a chromic material 22 responsive to contact with the wound and at least one article configured to introduce the chromatic material 22 to the wound 10. The kit also includes information for measuring a color change of the chromic material 22 as a result of the stimuli such as being in contact with the blood of the wound 10. FIGS. 4A and 4B illustrate exemplary embodiments of a chart or table of information 40, 46 for measuring color change of the chromic material.

In FIG. 4A, the information 40 includes a plurality of colors 42 corresponding to a plurality of temperatures 44. In response to identifying the color of the chromic material and, thus, measuring the color change based on ambient temperature of the chromic material prior to contacting a wound versus the subsequent temperature of the chromic material while contacting the wound the length of time may be determined as to how long the at least one article has been in contact with the wound. Alternatively, in FIG. 4B, the information 46 includes the plurality of colors 42 corresponding to a plurality of time periods 48. In one or more embodiments, some or all of both the temperatures 44 and time periods 48 could be combined on the same chart or table along with the corresponding colors 42. Referencing FIG. 4B, by identifying the color of the chromic material while the article has been in contact with the wound, a length of time may be determined as to how long the at least one article has been in contact with the wound.

In one or more embodiments, one or more of the expanded articles 30 may be removed from the wound 10 based on the color change of the chromic material 32 indicating how long the at least one expanded article 30 has been at least partially in contact with the wound 10 and then determining that one or more of the expanded articles 30 have been in contact with the wound 10 for too long. For example, in one or more embodiments, introducing the chromic material via at least one article into a wound may be performed by a first medical professional such as a paramedic and then removal of that at least one article with that chromic material from that wound based on the color change of the chromic material may be performed by a second medical professional such as a surgeon. Removal of the at least one article from the wound by the second medical professional may be performed without knowledge of when the first medical professional introduced the chromic material via the at least one article to the wound.

Figure 5:
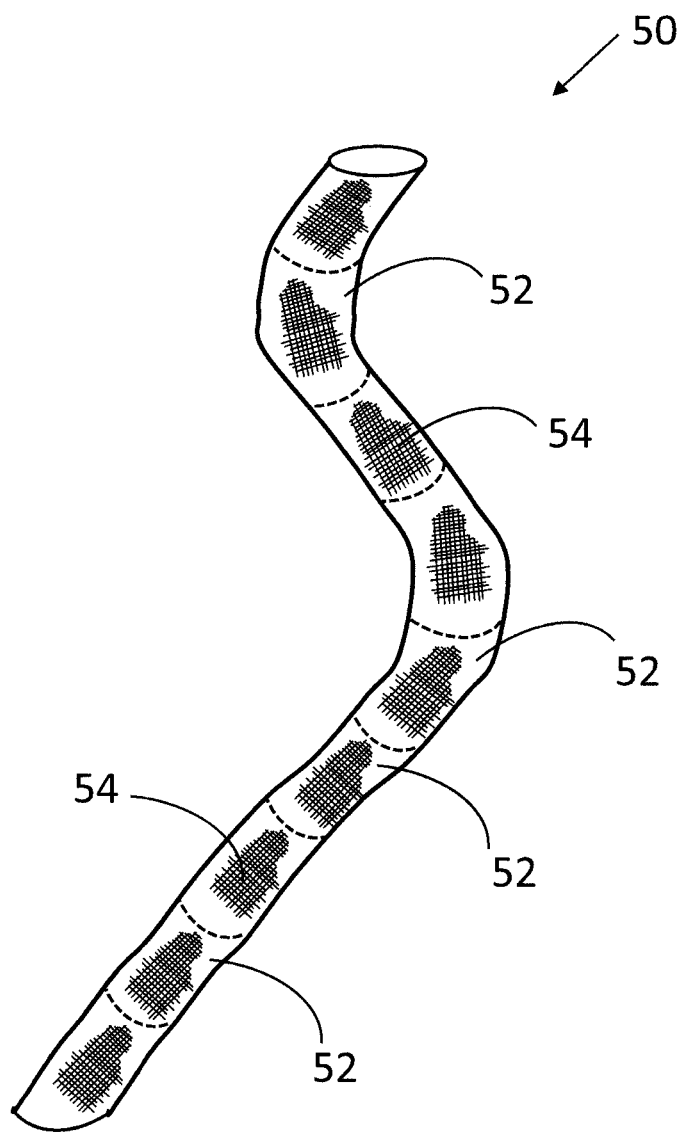
FIG. 5 depicts an elongated member define a plurality of individual liquid expandable articles having chromic material on each of the expandable articles according to one or more embodiments of the invention.

Turning now to FIGS. 5, 6, 7 and 8, FIG. 5 depicts an alternative embodiment of an article in the form of an elongated member 50 defining a plurality of individual liquid expandable articles 52 wherein the individual liquid-expandable articles 52 release stored mechanical energy and mechanically expand into expanded articles upon contact with liquid. Although the elongated member 50 in FIG. 5 is depicted with a particular number of expandable articles 52, the elongated member 50 may have any number of articles 52.

Figure 6:
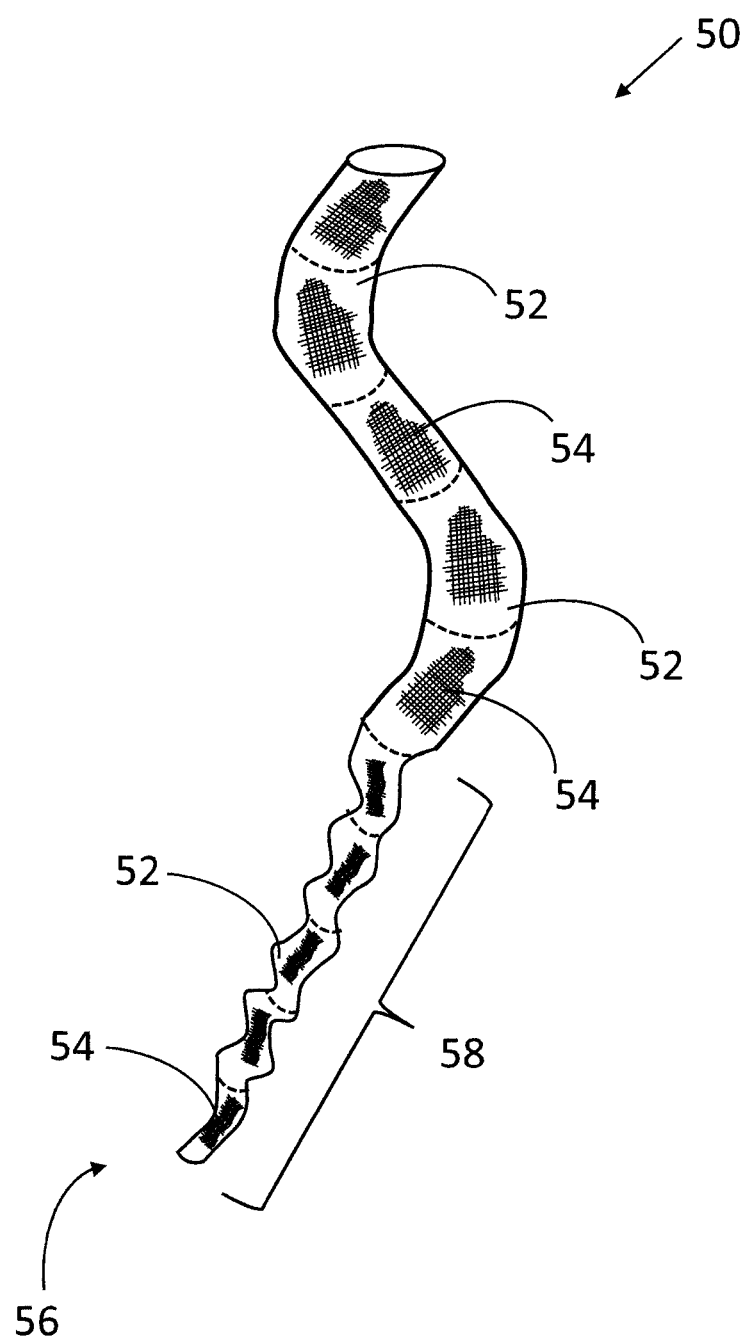
FIG. 6 depicts the elongated member of FIG. 5 where the distal end of the elongated member is manually crumpled according to one or more embodiments of the invention.
Figure 7:
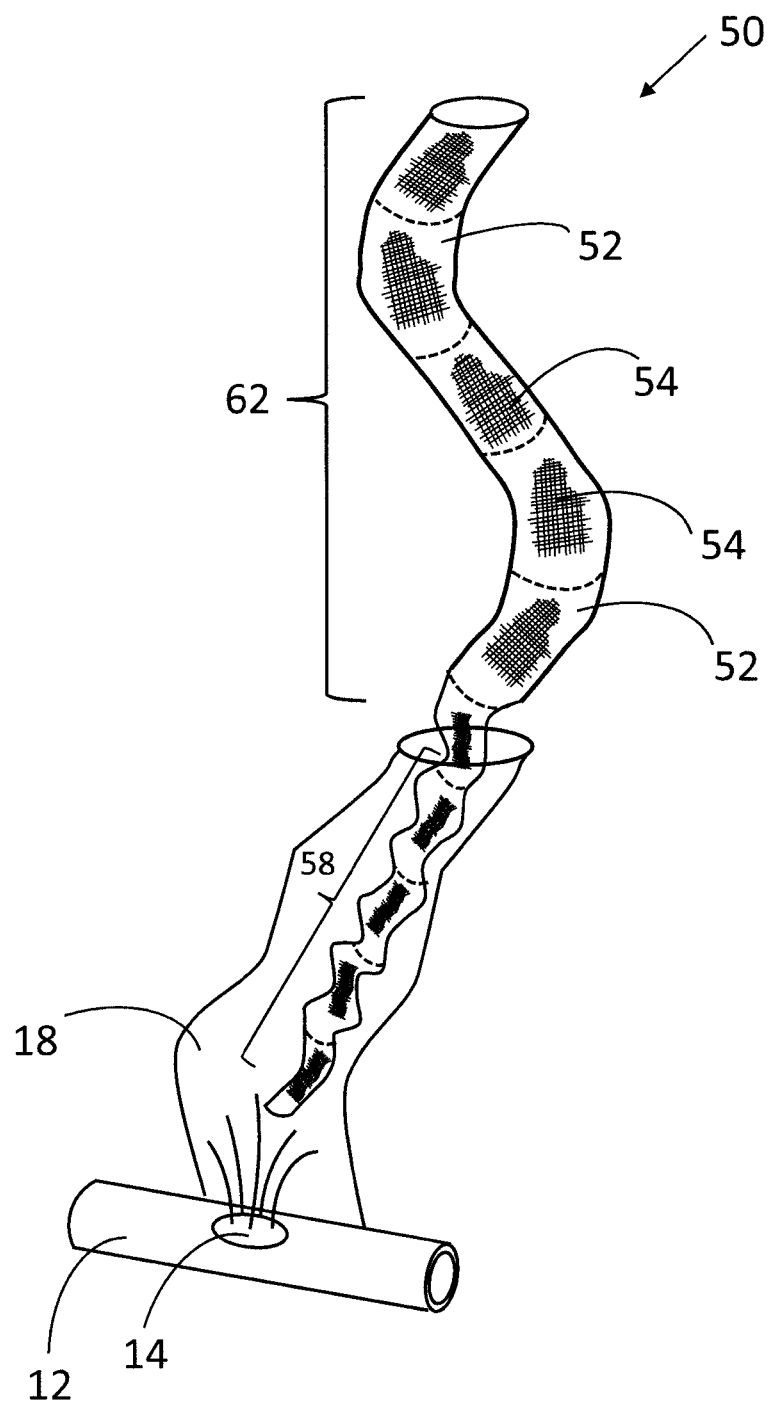
FIG. 7 depicts the elongated member of FIGS. 5 and 6 where the crumpled distal end of the elongated member has been received within a puncture wound according to one or more embodiments of the invention.
Figure 8:
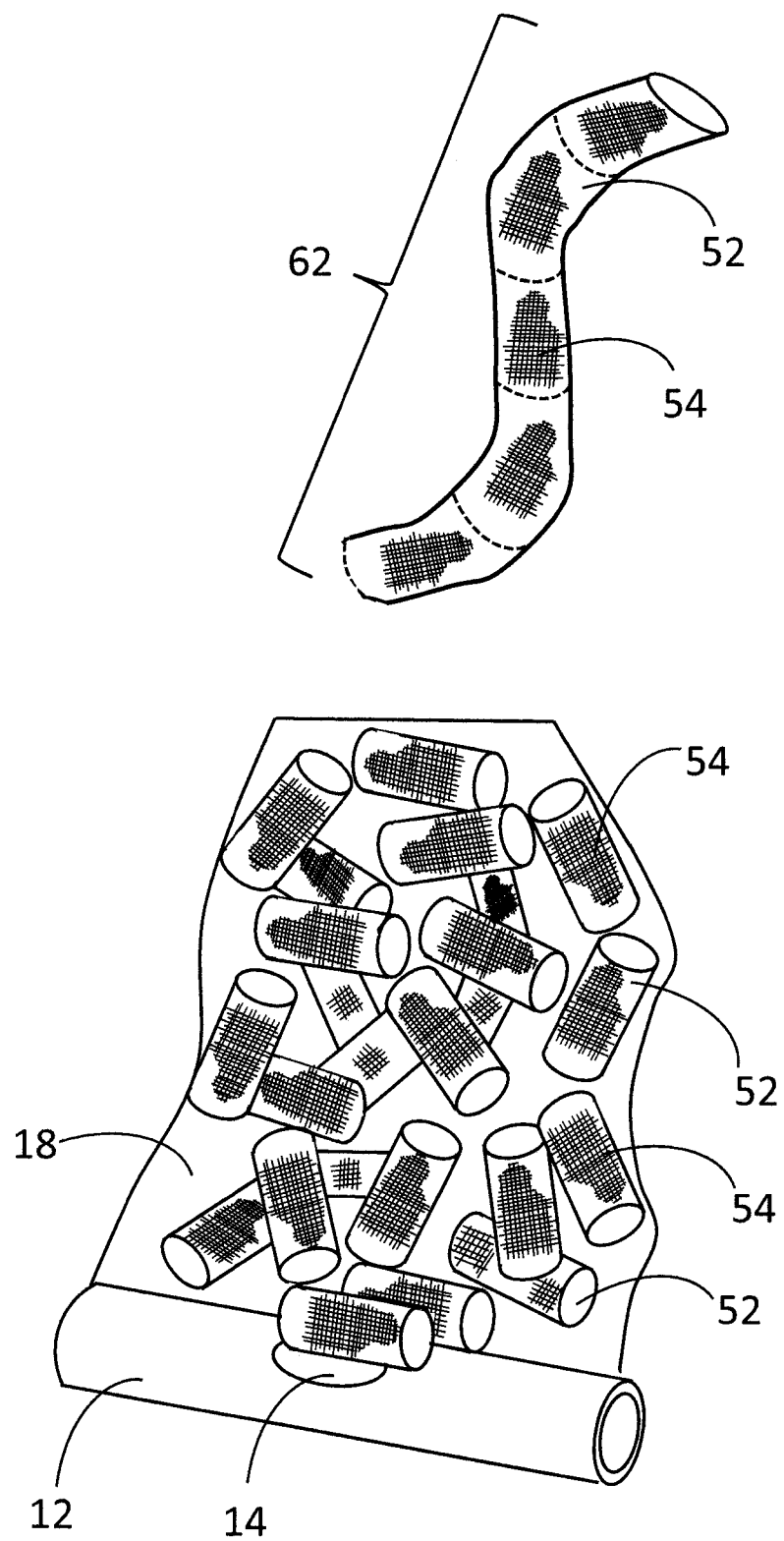
FIG. 8 depicts the distal end of the elongated member within the puncture wound separated from the remainder of the elongated member and the individual liquid expandable articles within the puncture wound separated from one another according to one or more embodiments of the invention.

The elongated member 50 also includes chromic material 54 on all or on one or more of the articles 52. Then the elongated member 50 may be configured to be at least partially received within the wound 10. For example, FIG. 6 depicts a distal end 56 of the elongated member 50 of FIG. 5 where a portion 58 of the distal end 56 of the elongated member 50 is manually squeezed, crumpled, crushed or otherwise reduced in size about a circumference or diameter such that the distal end 56 is then sized to be received inside or within the wound 10 as shown in FIG. 7. The length of the portion 58 of the elongated member 50 may be determined by estimating the depth of the wound 10. FIG. 8 then also shows a portion 62 of the plurality of the individual liquid-expandable articles 52 of the elongated member 50 remaining outside the wound 10. The distal end 56 of the elongated member 50 corresponding with the portion 58 received inside the wound 10 may be manually separated from the other portion 62 of the elongated member 50 not in contact with the wound 10 and remaining outside or exterior to the wound 10 by pulling apart, stretching, tearing, ripping or other suitable method of separating the two portions 58, 62 from one another.

Upon being received within the wound 10, all or some of the articles 52 then mechanically separate from one another. For example, the articles 52 affected by stimuli, such as coming into contact with liquid or blood, separate from one another due to the stored mechanical energy and mechanical expansion into the expanded articles. The articles 52 also separate from one another as a result of becoming obstructed or restricted against one another or against the sides of the cavity 18 while expanding to fill the cavity 18 of the wound 10. Alternatively, the articles 52 could be held together by a liquid soluble adhesive that dissolves upon contact with liquids such as blood. In one or more embodiments, the articles 52 separate from one another as a result of the portion 58 of the elongated member being pushed into the wound 10 and getting bent against itself within the wound 10.

In one or more embodiments, one or more of the articles 52 once expanded may be removed from the wound 10 based on the color change of the chromic material 54 indicating how long the at least one article 52 has been at least partially in contact with the wound 10 and then determining that one or more of the articles 52 after being expanded has then been in contact with the wound 10 for too long.

In one or more embodiments, a distal end of the portion 62 may also be manually squeezed, crumpled, crushed or otherwise reduced in size about a circumference or diameter such that another portion of the distal end 62 is then sized to be received inside or within wound 10 or a second or different wound. The portion of the distal end 62 within the wound may then be manually separated from yet another portion of the plurality of articles 52 not in contact with the wound and still remaining outside or exterior to the wound by pulling apart, stretching, tearing, ripping or other suitable method of separation.

Figure 9:
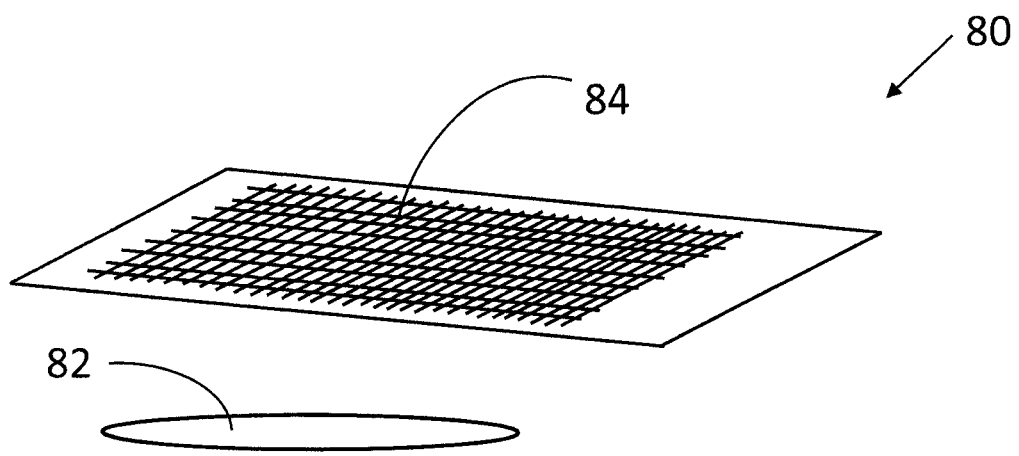
FIG. 9 depicts a wound dressing having chromic material over a wound according to one or more embodiments of the invention.
Figure 10:
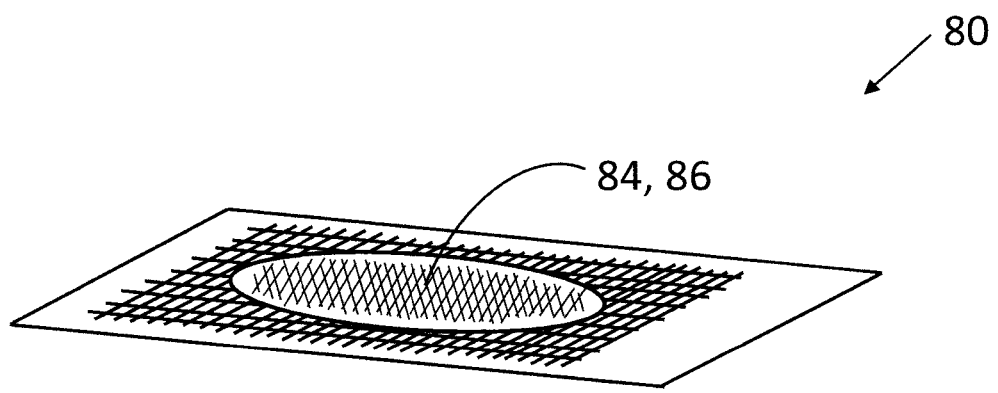
FIG. 10 depicts the wound dressing of FIG. 9 in contact with the wound where the chromic material has changed color according to one or more embodiments of the invention.

FIG. 9 depicts an alternative embodiment of an article configured as a wound dressing 80 having chromic material 84 over a wound 82. The wound dressing may be for example, but not limited to, a cloth dressing and wound 82 may be, for example, but not limited to, an open wound or an abrasion. In one or more embodiments, the wound dressing 80 may be pre-cut or in the form of a roll and the chromic material may by sprayed or pasted on after assessing the wound 82. Also, in one or more embodiments, the wound dressing 80 may be a foam combined with the chromic material 84. FIG. 10 then depicts the wound dressing 80 of FIG. 9 in contact with the wound 82 such that all or part of the chromic material 84 has had a color change 86 as a result of stimuli associated with the wound 82.

In one or more embodiments, the wound dressing 80 may be removed from the wound 82 based on the color change 86 of the chromic material 84 indicating how long the wound dressing 80 has been at least partially in contact with the wound 82 and then determining that the wound dressing 80 has been in contact with the wound 82 for too long.

Figure 11:
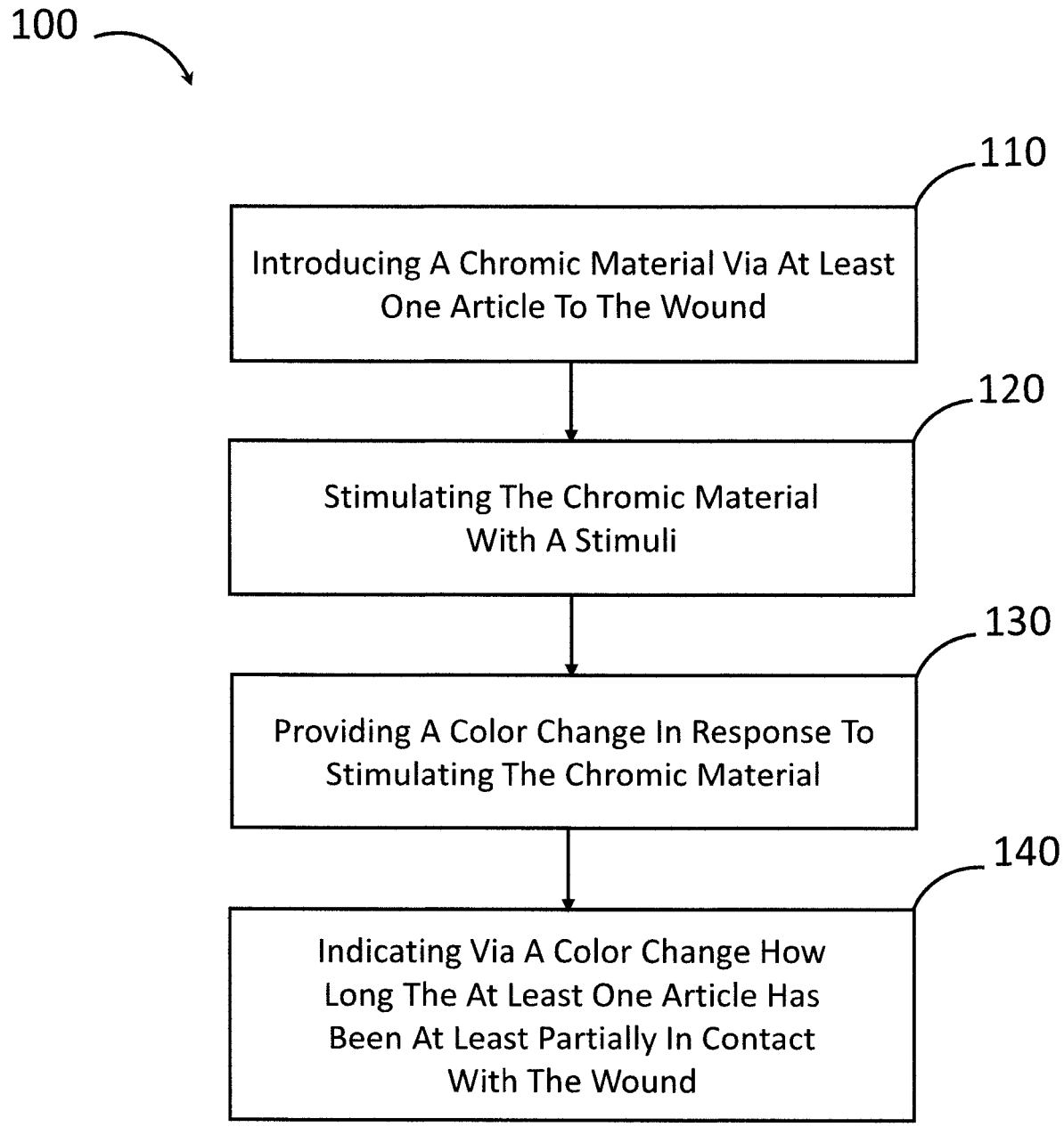
FIG. 11 is a flow diagram illustrating a method for dressing a wound according to one or more embodiments of the invention.

FIG. 11 depicts a flow diagram of a method for dressing a wound according to one or more embodiments of the invention. The method 100 includes process block 110 for introducing a chromic material via at least one article to the wound and process block 120 for stimulating the chromic material with a stimuli. The method 100 then includes process block 130 for providing a color change in response to stimulating the chromic material and process block 140 for indicating via a color change of the chromic material how long the at least one article has been at least partially in contact with the wound.

The method 100 may also include one or more other process blocks. In one or more embodiments, the method 100 can include indicating where the at least one article is within the wound. The method 100 can also include measuring the color change from information that include a plurality of colors corresponding to a plurality of time periods where, in response to measuring the color change, a length of time the at least one article has been in contact with the wound is determined. In one or more embodiments, indicating via the color change includes providing a first color change in response to initial contact of the at least one article with the wound and then subsequently providing a second color change in response to prolonged contact of the at least one article with the wound. Also, in one or more embodiments, the at least one article includes an elongated member defining the plurality of individual liquid expandable articles. The method 100 may also include manually crumpling a distal end of the elongated member such that a portion of the plurality of individual liquid expandable articles are sized to be received within the wound. The method 100 may then include manually separating the crumpled distal end from another portion of the elongated member not in contact with the wound.

The method 100 may also include crumpling a distal end of the other portion of the elongated member such that another portion of the plurality of individual liquid expandable articles are sized to be received within a second wound. Then the method 100 may include manually separating the crumpled distal end of the other portion of the elongated member from yet another portion of the elongated member not in contact with the wound.

The method 100 may also include removing the at least one article from the wound based on the color change of the chromic material indicating how long the at least one article has been at least partially in contact with the wound.

Figure 12A:
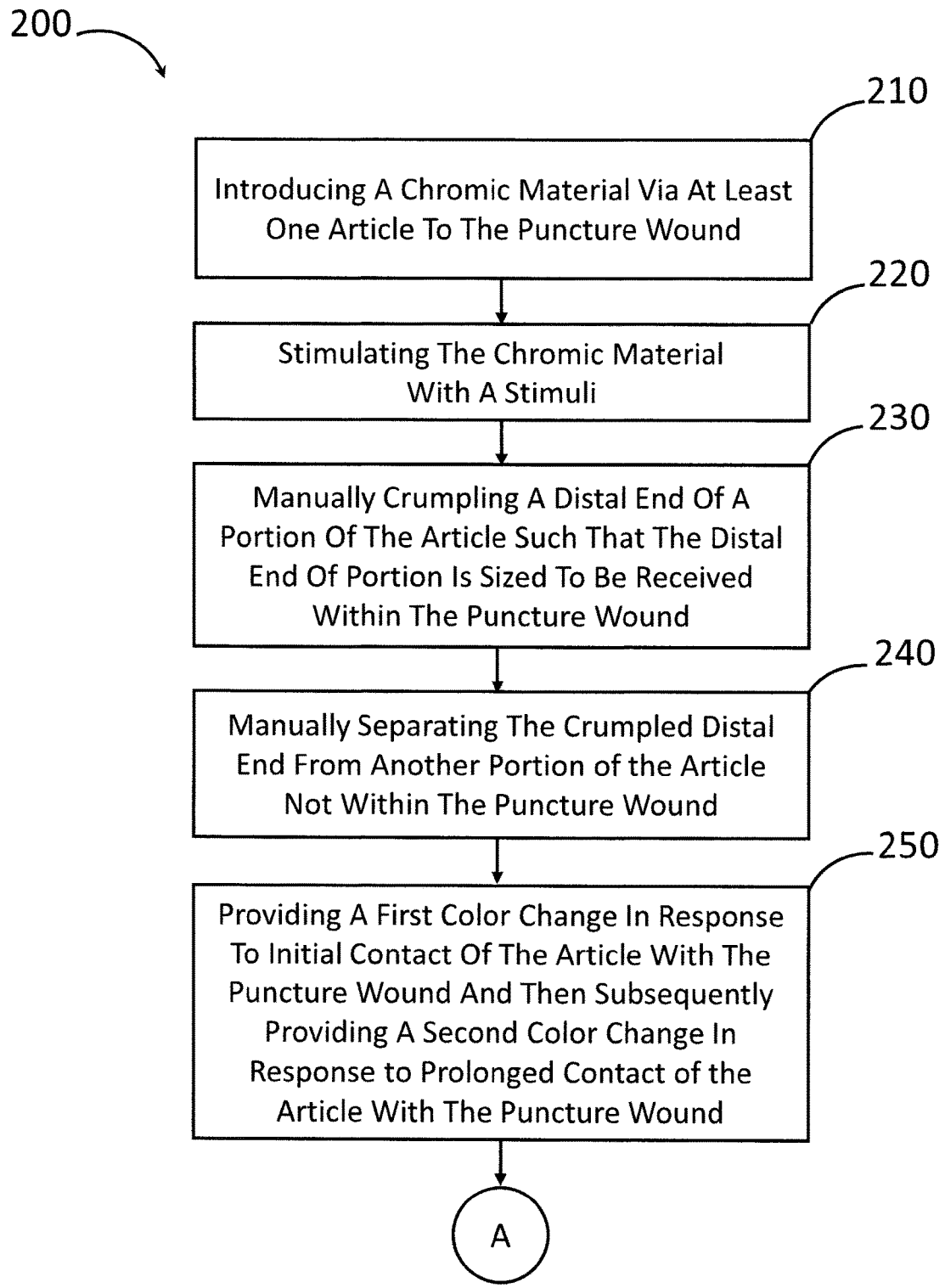
FIGS. 12A and 12B are a flow diagram illustrating an alternative method for dressing a wound according to one or more embodiments of the invention.
Figure 12B:
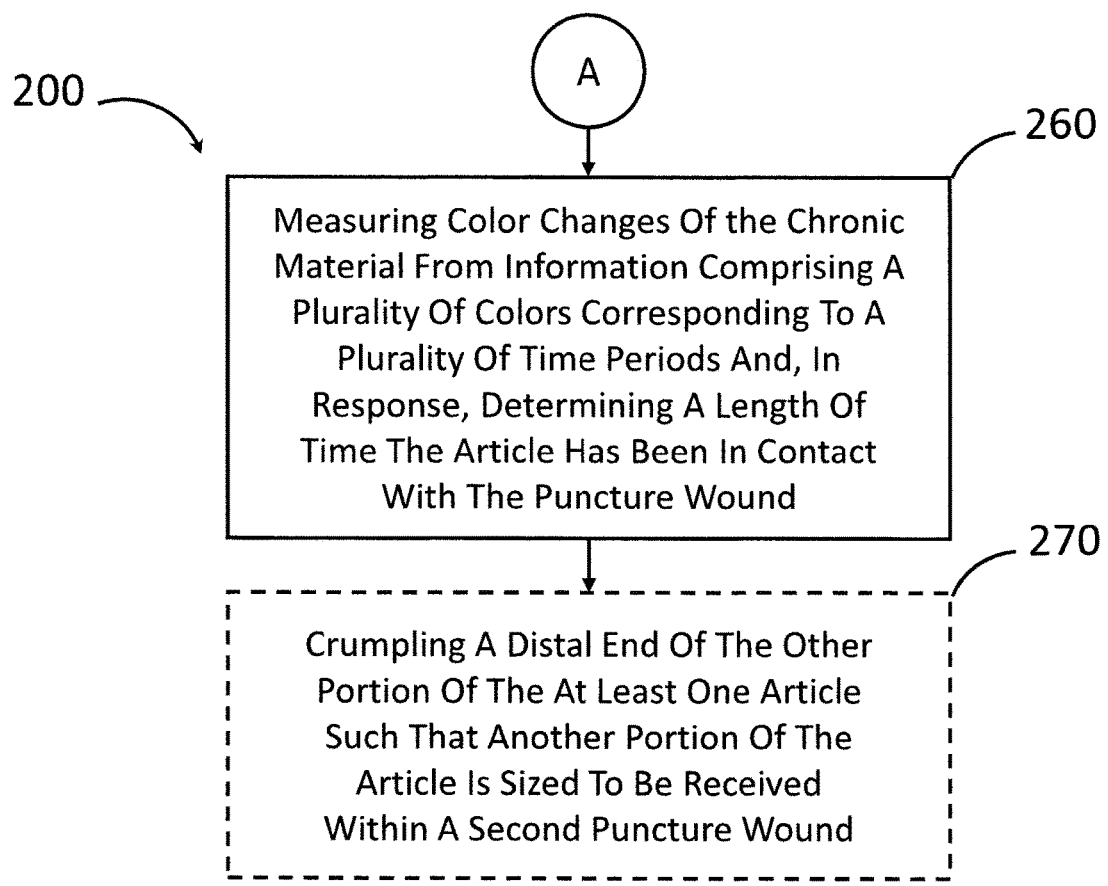

FIGS. 12A and 12B depict a flow diagram of another method for dressing a wound according to one or more embodiments of the invention. The method 200 includes process block 210 for introducing a chromic material via at least one article to the puncture wound and process block 220 for stimulating the chromic material with a stimuli. The method 200 also includes process block 230 for manually crumpling a distal end of a portion of the at least one article such that the distal end of the portion is sized to be received within the puncture wound and process block 240 for manually separating the crumpled distal end from another portion of the at least one article not within the puncture wound. The method 200 includes process block 250 for providing a first color change of the chromic material in response to initial contact of the at least one article with the puncture wound and then subsequently providing a second color change of the chromic material in response to prolonged contact of the at least one article with the wound. Next, the method 200 includes process block 260 for measuring color changes of the chromic material from information comprising a plurality of colors corresponding to a plurality of time periods and, in response, determining a length of time the at least one article has been in contact with the puncture wound.

The method 200 may also include one or more other process blocks. In one or more embodiments, the method 200 can include process block 270 for crumpling a distal end of the other portion of the at least one article such that another portion of the at least one article is sized to be received within a second puncture wound. The method 200 can also include removing the at least one article from the puncture wound based on the color change of the chromic material indicating how long the at least one article has been at least partially in contact with the wound. In one or more embodiments, introducing the chromic material via the at least one article to the puncture wound is performed by a first medical professional and removing the at least one article from the puncture wound based on the color change of the chromic material is performed by a second medical professional. Also, in one or more embodiments, removing the at least one article from the puncture wound by the second medical professional is performed without knowledge of when the first medical professional introduced the chromic material via the at least one article to the puncture wound.

Additional processes may also be included. It should be understood that the processes depicted in FIGS. 11, 12A and 12 B represent illustrations, and that other processes may be added or existing processes may be removed, modified, or rearranged without departing from the scope and spirit of the present disclosure.

In some alternative implementations, the functions noted in the process blocks may occur out of the order noted in the Figures. For example, two blocks shown in succession may, in fact, be executed substantially concurrently, or the blocks may sometimes be executed in the reverse order, depending upon the functionality involved.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of dressing a wound, comprising:
directly connecting a plurality of liquid-expandable articles at opposite ends of the plurality of liquid-expandable articles to define an elongated member, wherein each of the plurality of liquid-expandable articles are separable from one another at their opposite ends;

receiving and retaining a distal end of the elongated member into a wound while another portion of the elongated member remains outside of the wound, the plurality of liquid-expandable articles of the distal end of the elongated member remaining directly connected together while being received inside of the wound;

inserting a chromic material into the wound with each of the liquid-expandable articles of the distal end of the elongated member in response to being received inside of the wound;

contacting the liquid-expandable articles inside the wound with liquid from inside the wound; and in response to contact with the liquid inside the wound, the liquid-expandable articles releasing stored mechanical energy at their ends, separating from one another at their ends, and mechanically expanding into expanded articles.

2. The method of claim 1 further comprising, after the distal end has been received and retained inside the wound, manually separating the other portion of the elongated member remaining outside of the wound from the plurality of the liquid-expandable articles being retained inside the wound.

3. The method of claim 2 further comprising manually reducing the liquid-expandable articles of at least a portion of the distal end such that the at least a portion of the distal end is sized to be received inside the wound.

4. The method of claim 3 wherein manual reducing the liquid-expandable articles of at least a portion of the distal end comprises manually reducing a diameter of the liquid-expandable articles of at least a portion of the distal end to receive the distal end inside the wound.

5. The method of claim 4 wherein manually reducing a diameter of the liquid-expandable articles of at least a portion of the distal end to receive the distal end inside the wound comprises manually crumpling the distal end of the elongated member to receive the distal end inside the wound.

6. The method of claim 2 wherein manually separating the other portion of the elongated member comprises tearing the other portion of the elongated member remaining outside of the wound from the liquid-expandable articles being retained inside the wound.

7. The method of claim 1 further comprising stimulating the chromic material with a stimuli.

8. The method of claim 7 further comprising providing a color change in response to stimulating the chromic material.

9. The method of claim 1 further comprising receiving and retaining a distal end of the other portion of the elongated member into a second wound while yet another portion of the other portion of the elongated member remains outside of the second wound.

10. The method of claim 1 wherein receiving and retaining the distal end of the elongated member in the wound comprises determining a depth of the wound with the distal end of the elongated member such that the distal end corresponds with the depth of said wound.

11. A method for dressing a puncture wound, the method comprising the steps of:
directly connecting a plurality of liquid-expandable articles at opposite ends of the plurality of liquid-expandable articles to define an elongated member, wherein each of the plurality of liquid-expandable articles are separable from one another at their opposite ends;

receiving and retaining a distal end of the elongated member into a wound while another portion of the elongated member remains outside of the wound, the plurality of liquid-expandable articles of the distal end of the elongated member remaining directly connected together while being received inside of the wound;

inserting a chromic material into the wound with each of the liquid-expandable articles of the distal end of the elongated member in response to being received inside of the wound;

after the distal end has been received and retained inside the wound, manually separating the other portion of the elongated member remaining outside of the wound from the plurality of the liquid-expandable articles being retained inside the wound, contacting the liquid-expandable articles inside the wound with liquid from inside the wound; and in response to contact with the liquid inside the wound, the liquid-expandable articles releasing stored mechanical energy at their ends, separating from one another at their ends, and mechanically expanding into expanded articles.

12. The method of claim 11 further comprising manually reducing the liquid-expandable articles of at least a portion of the distal end such that the at least a portion of the distal end is sized to be received inside the wound.

13. The method of claim 12 wherein manual reducing the liquid-expandable articles of at least a portion of the distal end comprises manually reducing a diameter of the liquid-expandable articles of at least a portion of the distal end to receive the distal end inside the wound.

14. The method of claim 13 wherein manually reducing a diameter of the liquid-expandable articles of at least a portion of the distal end to receive the distal end inside the wound comprises manually crumpling at least a portion of the distal end of the elongated member to receive the distal end inside the wound.

15. The method of claim 11 further comprising receiving and retaining a distal end of the other portion of the elongated member into a second wound while yet another portion of the other portion of the elongated member remains outside of the second wound.

16. The method of claim 11 wherein separating other portion of the elongated member comprises tearing the other portion of the elongated member remaining outside of the wound from the liquid-expandable articles being retained inside the wound.

17. The method of claim 11 wherein receiving and retaining the distal end of the elongated member in the wound comprises determining a depth of the wound with the distal end of the elongated member such that the distal end corresponds with the depth of said wound.

18. The method of claim 11 further comprising removing the distal end of the elongated member from the wound based on a color change of the chromic material indicating how long the liquid-expandable members of the distal end have been in contact with the wound.

* * * * *